US011621282B2

(12) United States Patent
Jung et al.

(10) Patent No.: US 11,621,282 B2
(45) Date of Patent: Apr. 4, 2023

(54) MULTIPLEXING SIGNAL PROCESSING DEVICE BASED ON SEMICONDUCTOR PASSIVE ELEMENT

(71) Applicant: SOGANG UNIVERSITY RESEARCH & BUSINESS DEVELOPMENT FOUNDATION, Seoul (KR)

(72) Inventors: Ji Woong Jung, Seoul (KR); Yong Choi, Seoul (KR); Kun Tai Park, Gunpo-si (KR)

(73) Assignee: SOGANG UNIVERSITY RESEARCH & BUSINESS DEVELOPMENT FOUNDATION, Seoul (KR)

( * ) Notice: Subject to any disclaimer, the term of this patent is extended or adjusted under 35 U.S.C. 154(b) by 138 days.

(21) Appl. No.: 17/424,740

(22) PCT Filed: Jan. 14, 2020

(86) PCT No.: PCT/KR2020/000659
§ 371 (c)(1),
(2) Date: Jul. 21, 2021

(87) PCT Pub. No.: WO2020/153648
PCT Pub. Date: Jul. 30, 2020

(65) Prior Publication Data
US 2022/0139971 A1    May 5, 2022

(30) Foreign Application Priority Data

Jan. 21, 2019  (KR) .................. 10-2019-0007605

(51) Int. Cl.
*H01L 27/144* (2006.01)
*G01J 1/44* (2006.01)
*A61B 6/00* (2006.01)

(52) U.S. Cl.
CPC ........ *H01L 27/1446* (2013.01); *A61B 6/4208* (2013.01); *G01J 1/44* (2013.01)

(58) Field of Classification Search
CPC . H01L 27/1446; A61B 6/4208; A61B 6/5205; A61B 6/42; A61B 6/037; A61B 6/4258; G01J 1/44; G01T 1/20184
See application file for complete search history.

(56) References Cited

U.S. PATENT DOCUMENTS 8,247,780 B2 * 8/2012 Zhang ................... G01T 1/1642
250/370.11
8,575,534 B2 * 11/2013 Olcott ................... G01J 1/4228
250/214 R (Continued)

FOREIGN PATENT DOCUMENTS

JP    2014168202    9/2014
KR    101815290    1/2018

OTHER PUBLICATIONS

International Search Report—PCT/KR2020/000659 dated Apr. 16, 2020.

*Primary Examiner* — Seung C Sohn
(74) *Attorney, Agent, or Firm* — Cantor Colburn LLP

(57) ABSTRACT

Provided is a multiplexing signal processing device based on a passive element including a plurality of signal converters that respectively process a plurality of input signals and are arranged in a matrix consisting of N rows and M columns and include N signal converter blocks respectively connected to N row unit output terminals; and M signal converter blocks respectively connected to M column unit output terminals. The signal converters each include a first diode having an input terminal connected to an input signal node, a second diode having an input terminal connected to the input signal node, and a ground resistor coupled to the input signal node.

5 Claims, 8 Drawing Sheets

(56) References Cited

U.S. PATENT DOCUMENTS

| | | |
|---|---|---|
| 9,954,124 B1 | 4/2018 | Kuznetsov |
| 2013/0170616 A1 | 7/2013 | Mruthyunjaya et al. |
| 2013/0293296 A1 | 11/2013 | Proffitt |
| 2018/0091126 A1 | 3/2018 | Cheng et al. |

* cited by examiner

| | Resistor-Resistor | Resistor-Resistor-Resistor | Diode-Diode | Diode-Diode-Resistor |
|---|---|---|---|---|
| Crosstalk voltage (mV) | 27 | 23.9 | 20.4 | 15.6 |
| Crosstalk voltage STD (mV) | 3.5 | 3.3 | 5.1 | 3.2 |
| Crosstalk ratio (Amplitude mean/noise mean) | 0.22 | 0.29 | 0.046 | 0.037 |
| Rise time (ns) | 64 | 45 | 39 | 25 |
| Fall time (ns) | 744 | 339 | 260 | 160 |

| | Resistor-Resistor | Resistor-Resistor-Resistor | Diode-Diode | Diode-Diode-Resistor |
|---|---|---|---|---|
| Energy resolution (%) | 10.1 | 10.2 | 16.3 | 15.3 |
| Energy linearity (511 keV / 1275 keV) | 0.65 | 0.68 | 0.78 | 0.87 |
| Coincidence resolving time (ns) | 2.9 | 2.5 | 2.1 | 1.8 |

MULTIPLEXING SIGNAL PROCESSING DEVICE BASED ON SEMICONDUCTOR PASSIVE ELEMENT

BACKGROUND

1. Technical Field

The present disclosure relates to a multiplexing signal processing device, which may be used in a radiation image processing device, based on a semiconductor passive element.

2. Related Art

Radiation medical imaging equipment, which has been widely used recently, converts radiation into an optical signal, detects the optical signal, and obtains an image signal for an object. In this case, in order to provide accurate anatomical/physiological image information, a multi-channel pixel-type detector is used. For example, radiation imaging equipment such as a positron emission tomography (hereinafter, referred to as a "PET") or a gamma camera uses pixel-type optical sensors with a large number of channels per unit area to increase sensitivity. Due to the increase in channels, burden of signal processing in acquiring and processing data is increased.

For example, the PET diagnoses abnormalities in metabolism by imaging biological metabolic processes. The PET is configured with several scintillators arranged in a ring or polygon to detect γ-rays, a photodetector, and a signal processing unit.

In particular, a photodetector generally has a structure in which rectangular columnar scintillators are stacked in one or multiple stages, and the lower end of each of the scintillators includes a photoelectric element for processing a detected signal and other signal processors.

For the signal processor of the photodetector of the PET, multiplexing signal processing was performed by using resistive change division multiplexing or capacitive change division multiplexing, in the related art.

Multiplexing circuits that are currently widely used include discretized positioning circuit (DPC) which uses a method of determining a detected position by using a formula to a ratio of a current divided according to a position of an input signal, and a symmetric charge division circuit (SCD) which uses a method of determining a detection position by comparing differences between magnitudes of output signals of rows and columns according to the input signal, and use passive elements such as resistors or capacitors.

The DPC and SCD composed of arrangement of the passive elements have an advantage of low price due to a small circuit size and a simple circuit but has a disadvantage in that linearity of an output signal is reduced because a leakage current is generated according to a movement path of a current and the current decreases when passing through a passive element. Recently, an SCD type multiplexing circuit has been developed in which a resistor or a capacitor is replaced with a diode, and a circuit has been developed which can increase linearity of an output signal by reducing the amount of current that is reduced when passing through an element, but there are still disadvantages that a leakage current is generated and an energy resolution is reduced.

FIGS. 1A and 1B illustrate a commonly used multiplexing signal processing circuit.

A multiplexing processing device (DPC) based on a resistive change division circuit illustrated in FIG. 1A has a state in which a plurality of resistor elements is connected to each other in a matrix. The DPC based on the resistor dividing circuit has a great advantage of a high channel reduction ratio by reducing the number of N×N inputs to four outputs. However, the DPC circuit has a disadvantage in that a signal-to-noise ratio decreases as the number of channels increases and linearity decreases at an edge of an effective field of view of an image.

The multiplexing processing device (SCD) based on a capacitive change division circuit illustrated in FIG. 1B includes a plurality of capacitors coupled to respective optical sensors. The SCD reduces the number of N×N inputs to 2N outputs, and thus, a channel reduction ratio is not high but has an advantage of high linearity compared to the DPC. However, there is a disadvantage in that a signal-to-noise ratio is reduced due to a leakage current between channels divided into rows and columns.

SUMMARY

The present disclosure provides a multiplexing signal processing device capable of minimizing a leakage current.

The technical problems to be achieved by the present embodiment are not limited to the technical problems described above, and other technical problems may exist.

According to an aspect of the present disclosure, a multiplexing signal processing device based on a passive element includes a plurality of signal converters that respectively process a plurality of input signals and are arranged in a matrix consisting of N (N is a natural number) rows and M (M is a natural number) columns and include N signal converter blocks respectively connected to N row unit output terminals; and M signal converter blocks respectively connected to M column unit output terminals. The signal converters each include a first diode having an input terminal connected to an input signal node for receiving one of the plurality of input signals, a second diode having an input terminal connected to the input signal node, and a ground resistor coupled to the input signal node. An output terminal of the first diode of each of the signal converters arranged in the same row is connected to one of the row unit output terminals. An output terminal of the second diode of each of the signal converters arranged in the same column is connected to one of the column unit output terminals.

According to another aspect of the present disclosure, a radiation signal processing device includes a plurality of optical sensors configured to convert a scintillation signal, which is output from a scintillator unit that converts radiation into the scintillation signal, into an electrical signal; and a plurality of signal converters configured to process output signals of the plurality of optical sensors. The plurality of signal converters are arranged in a matrix consisting of N (N is a natural number) rows and M (M is a natural number) columns and include N signal converter blocks respectively connected to N row unit output terminals and M signal converter blocks respectively connected to M column unit output terminals, the signal converters each include a first diode having an input terminal connected to an input signal node for receiving one of output signals of the plurality of optical sensors, a second diode having an input terminal connected to the input signal node, and a ground resistor connected to the input signal node. An output terminal of the first diode of each of the signal converters arranged in the same row is connected to one of the row unit output terminals. An output terminal of the second diode of each of the signal converters arranged in the same column is connected to one of the column unit output terminals.

According to the present disclosure, it is possible to efficiently process a plurality of optical signals processed by a device for processing a radiographic image through a multiplexing signal processing device having a relatively simple structure. In particular, it is possible to maintain linear output signal characteristics which is a semiconductor passive device which is an advantage of using a diode by connecting a ground resistor to a diode-based multiplexing circuit, and it is possible to increase an energy resolution, a time resolution, energy linearity, and a signal-to-noise ratio by reducing a leakage current with the ground resistor.

BRIEF DESCRIPTION OF THE DRAWINGS

FIG. 5 is a diagram illustrating performance of the multiplexing signal processing device according to the embodiment of the present disclosure.

DETAILED DESCRIPTION OF THE EMBODIMENTS

Figure 1A:
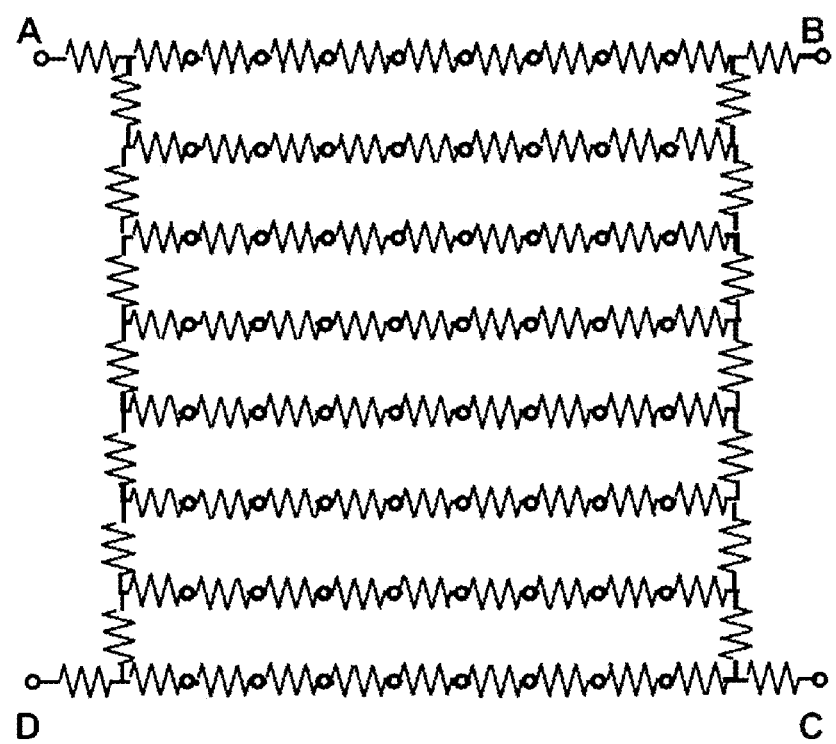
FIGS. 1A and 1B illustrate a commonly used multiplexing signal processing circuit.
Figure 1B:
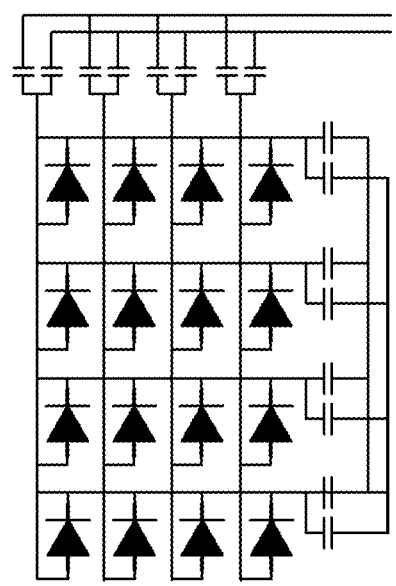

Hereinafter, embodiments of the present application will be described in detail with reference to the accompanying drawings such that those skilled in the art can easily implement the embodiments. However, the present application may be implemented in several different forms and is not limited to the embodiments described herein. In order to clearly describe the present application, portions irrelevant to the description are omitted in the drawings, and similar reference numerals are attached to similar portions throughout the specification.

Throughout the present specification, when a portion is "connected" to another portion, this includes not only a case of being "directly connected", but also a case of being "electrically connected" with another element interposed therebetween.

Throughout the present specification, when a member is described to be located "on" another member, this includes not only a case in which the member is in contact with a certain member but also a case in which another member is between the two members.

Throughout the present specification, when a portion "includes" a certain component, this means that other components may be further included therein, rather than excluding other components, unless otherwise stated. As used throughout the present specification, terms "about", "substantially", and the like are used in a sense at or close to a numerical value when presented with manufacturing and material tolerances inherent in the stated meaning, and are used to prevent an unconscionable infringer from unduly exploiting the disclosure in which precise or absolute figures are recited to aid understanding of the present application. A term "step of doing" or "step of" used throughout the present specification does not mean "step for".

Figure 2:
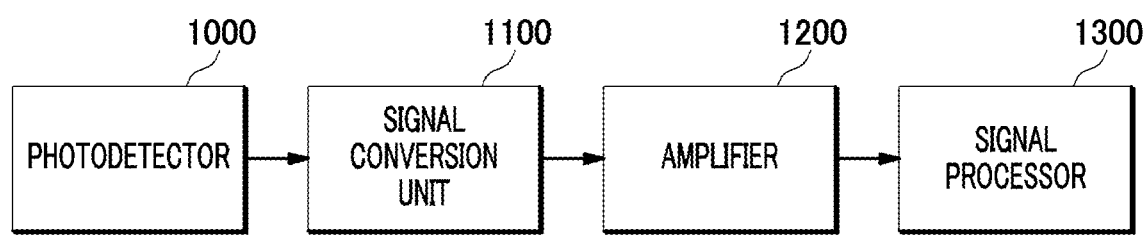
FIG. 2 is a block diagram illustrating a multiplexing signal processing device according to an embodiment of the present disclosure.

FIG. 2 is a block diagram illustrating a multiplexing signal processing device according to an embodiment of the present disclosure.

A multiplexing signal processing device 100 includes a photodetector 1000 and a signal conversion unit 1100. In addition, the multiplexing signal processing device 100 may further include an amplifier 1200 and a signal processor 1300.

The multiplexing signal processing device 100 is used in a radiation image processing device such as a positron emission tomography (PET) or a gamma camera and may be included in a corresponding device to function as a component.

The photodetector 1000 includes a plurality of optical sensors that convert a scintillation signal output from a scintillator for converting radiation into the scintillation signal into an electrical signal. In this case, the optical sensors may each include a photodiode, a semiconductor optical sensor, a photomultiplier tube, or the like.

The signal conversion unit 1100 includes a plurality of signal converters that are respectively coupled to the optical sensors of the photodetector 1000 and convert output signals of the optical sensors. Through this, radiographic image signals are multiplexed.

The amplifier 1200 amplifies a pulse signal output from the photodetector through the signal conversion unit and transmits the amplified pulse signal to the signal processor 1300. The amplifier 1200 may be implemented by various types of commonly used amplifier circuits.

The signal processor 1300 analyzes position information of the optical sensors from which respective pulse signals are output based on characteristics of respective pulse amplified by the amplifier 1200.

Figure 3:
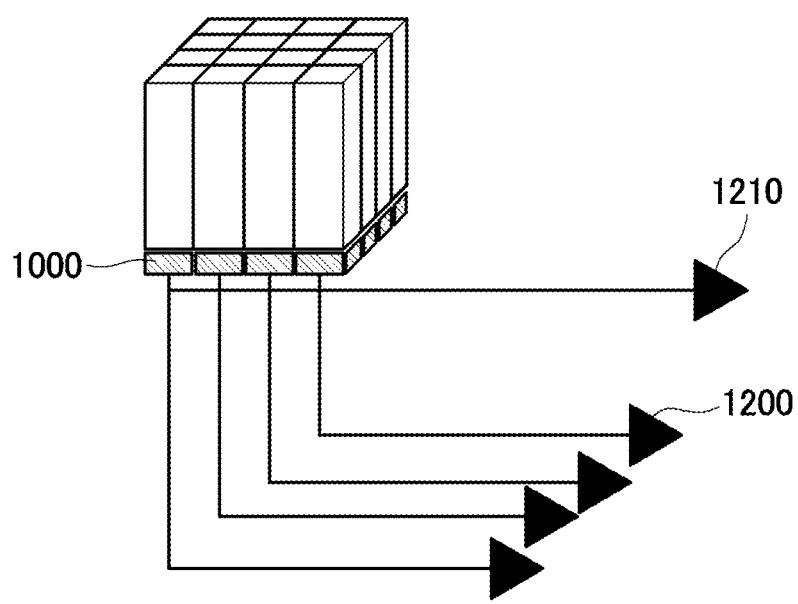
FIG. 3 is a diagram illustrating the multiplexing signal processing device according to the embodiment of the present disclosure.
Figure 4:
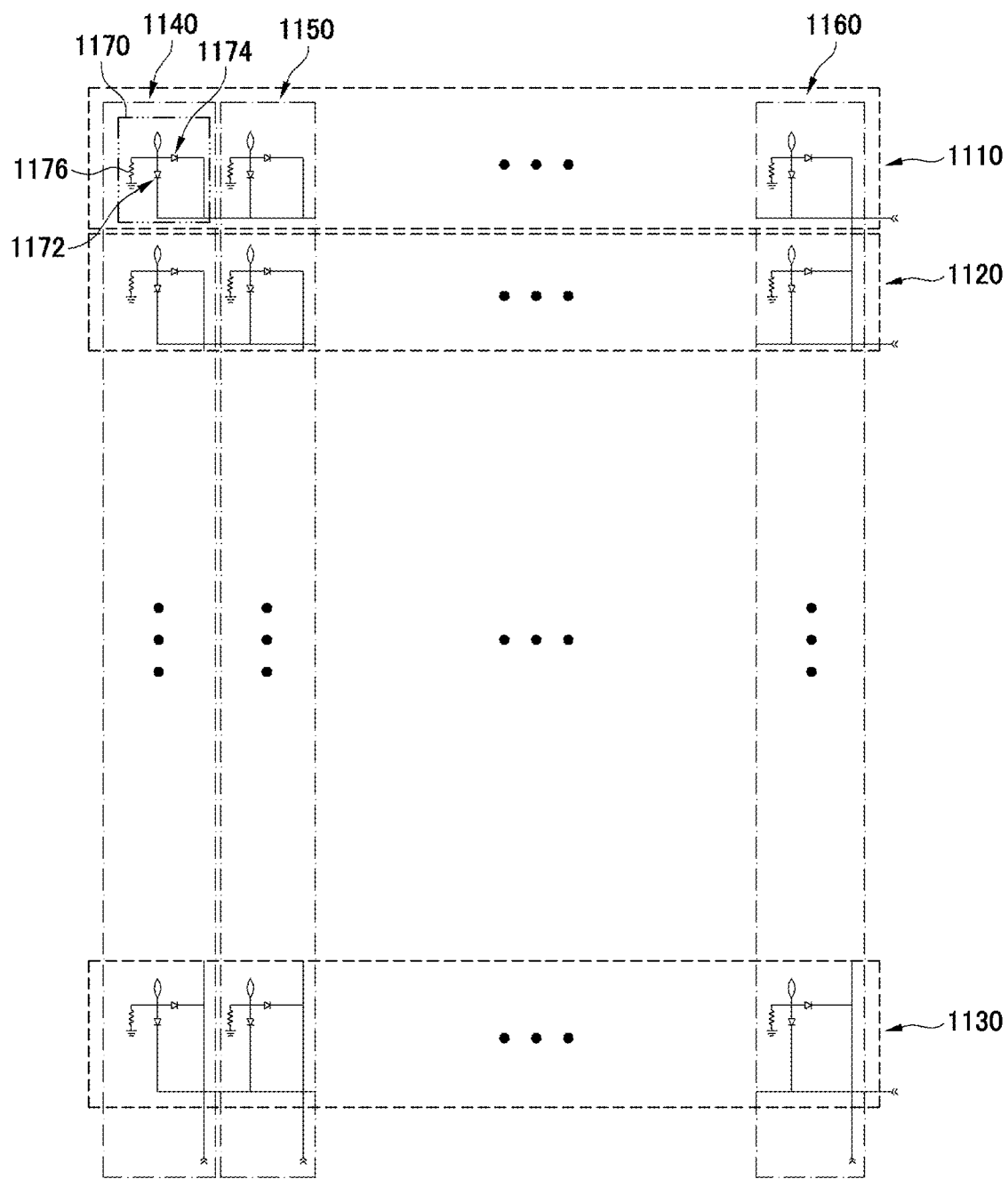
FIG. 4 is a diagram illustrating a configuration of a signal converter according to an embodiment of the present disclosure.
Figure 6:
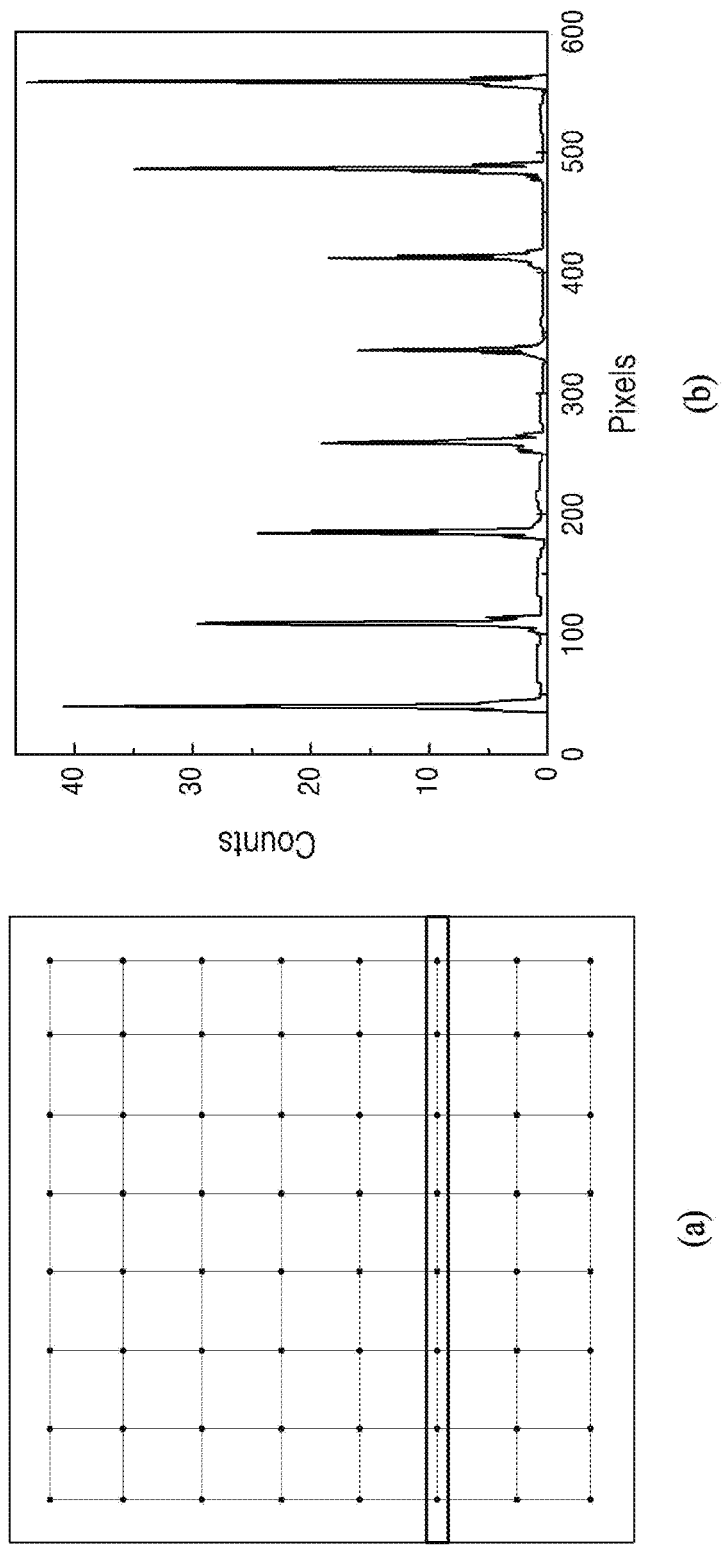
FIGS. 6 to 8 are diagrams of a flood histogram and a profiling result illustrating the performance of the multiplexing signal processing device according to the embodiment of the present disclosure.
Figure 7:
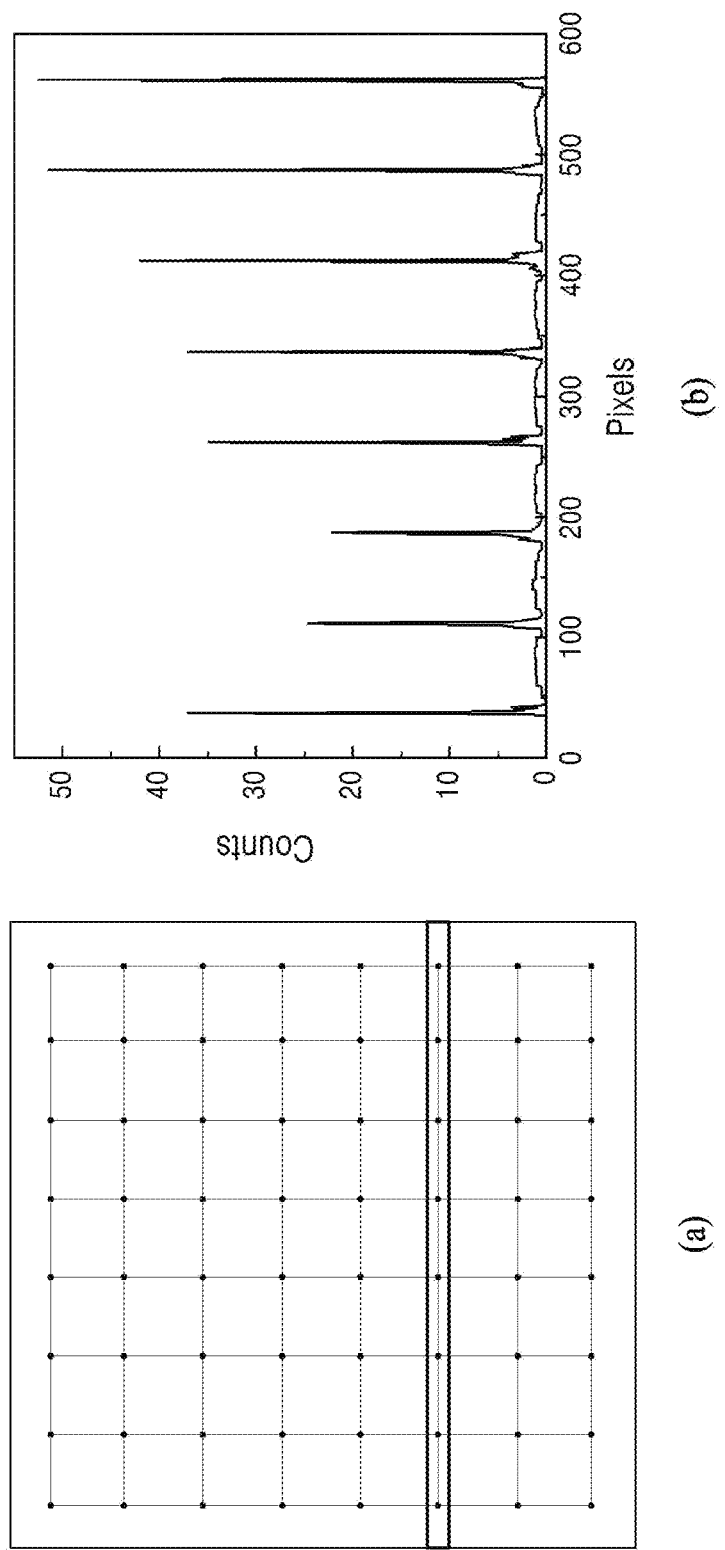
Figure 8:
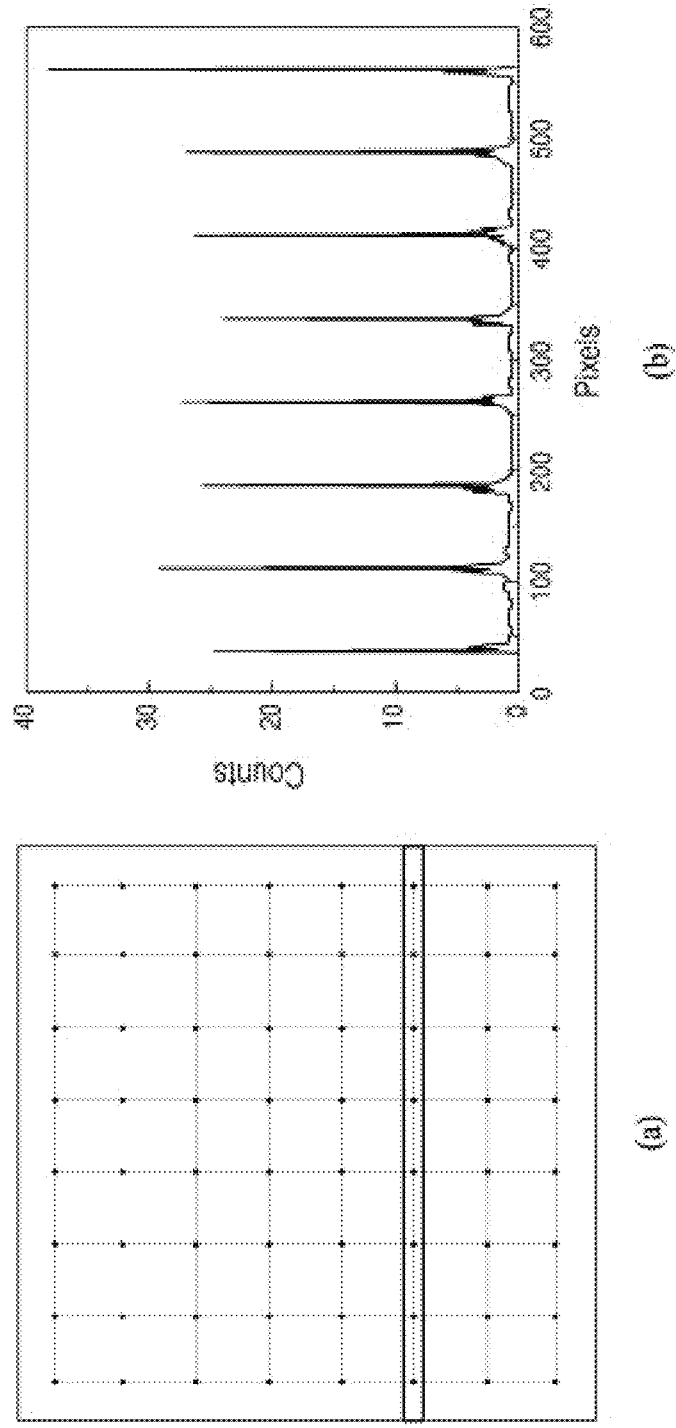

FIG. 3 is a diagram illustrating the multiplexing signal processing device according to the embodiment of the present disclosure, and FIG. 4 is a diagram illustrating a configuration of the signal conversion unit according to an embodiment of the present disclosure.

As illustrated in FIG. 3, the photodetector 1000 including the optical sensors is disposed at a lower end of a scintillator, a plurality of channels including the optical sensors are arranged, and signals passing through the respective channels are transmitted to the signal processor 1300 through the amplifier 1200 or 1210.

In addition, as illustrated in FIG. 4, the plurality of signal converters are arranged in a matrix consisting of N (N is a natural number) rows and M (M is a natural number) columns and include N signal conversion unit blocks 1110, 1120, and 1130 respectively connected to N row unit output terminals and M signal conversion unit blocks 1140, 1150, and 1160 respectively connected to M (M is a natural number) column unit output terminals.

For example, the plurality of signal converters may be arranged in an 8×8 matrix, which is an example, and the plurality of signal converters may be arranged in various forms.

In this case, a signal converter 1170 includes a first diode 1172 having an input terminal connected to an input signal node for receiving an input signal, a second diode 1174 having an input terminal connected to the input signal node; and a ground resistor 1176 connected to the input signal node.

Output terminals of the first diodes 1172, which are arranged in the same row, of each of the signal conversion unit blocks 1110, 1120, and 1130 are connected to the row unit output terminal. Likewise, Output terminals of the second diodes 1172, which are arranged in the same column, of each of the signal conversion unit blocks 1140, 1150, and 1160 are connected to the column unit output terminal.

When a signal is input to the input signal node of each channel, the signal is output to an x-axis line and an y-axis line, and only a small amount of leakage current exceeding a reverse voltage of a diode can pass therethrough. When the signal exceeding the reverse voltage is input, a leakage current occurs in a surrounding signal, and in this case, a ground resistor provides a ground path such that the leakage current exceeding the reverse voltage does not move to x and y axes of other adjacent signal converters, and thus, the amount of leakage current is effectively reduced.

FIG. 5 is a diagram illustrating performance of the multiplexing signal processing device according to the embodiment of the present disclosure.

FIG. 5 illustrates experimental results for comparison when resistors are respectively connected to a row and a column of the input signal node, when the resistors are respectively connected to the row and the column of the input signal node and a ground resistor is additionally connected thereto, when diodes are respectively connected to the row and the column of the input signal node, and when the diodes are respectively connected to the row and column of the input signal node and the ground resistor is additionally connected thereto.

It can be seen that a crosstalk voltage of a multiplexing circuit according to the present disclosure is the smallest compared to other configurations. In addition, it can be seen that a rise time and a fall time of each signal are the fastest in the multiplexing circuit according to the present disclosure.

In addition, it can be seen that the multiplexing circuit according to the present disclosure has very excellent energy resolution, energy linearity, and coincidence resolving time compared to other technologies.

FIGS. 6A to 8B are diagrams of a flood histogram and a profiling result illustrating performance of the multiplexing signal processing device according to the embodiment of the present disclosure.

FIGS. 6A and 6B illustrates a flood histogram of 64 channels which is obtained and an image when the resistors are respectively connected to the row and column of the input signal node and the ground resistor is additionally connected (resistor-resistor), FIGS. 7A and 7B illustrates a flood histogram of 64 channels which is obtained and an image when the diodes are respectively connected to the row and column of the input signal node (diode-diode), and FIGS. 8A and 8B illustrates a flood histogram of 64 channels which is obtained and an image when diodes are respectively connected to the row and column of the input signal node and the ground resistor is additionally connected (diode-diode-resistor).

In this case, FIGS. 6A, 7A, and 8A illustrate flood histograms of 64 channels obtained by using Na-22 dotted line circles to compare results of coordinate mapping and an image, and FIGS. 6B, 7B, and 8B illustrate profiles of a peak-to-valley ratio (PVR) obtained by profiling a portion illustrated as rectangles in the flood histogram.

7.9 is obtained in FIG. 6B and 16.1 is obtained in FIG. 7B and 20.6 is obtained in FIG. 8B, and thus, it can be seen that the diode-diode-resistor circuit corresponding to the multiplexing signal processing device is increased by 61% and 21% compared to the resistor-resistor circuit and the diode-diode circuit, respectively.

The foregoing description of the present application is for illustration, and those skilled in the art to which the present application pertains will understand that the present application can be easily modified into other specific forms without changing the technical idea or essential features of the present application. Therefore, it should be understood that the embodiments described above are illustrative in all respects and not restrictive. For example, each component described as a single type may be implemented in a distributed form, and likewise components described as a distributed form may be implemented in a combined form.

The scope of the present application is indicated by the following claims rather than the above detailed description, and all changes or modifications derived from the meaning and scope of the claims and their equivalent concepts should be construed as being included in the scope of the present application.

What is claimed is:

1. A multiplexing signal processing device based on a passive element, comprising:
   a plurality of signal converters that respectively process a plurality of input signals and are arranged in a matrix consisting of N (N is a natural number) rows and M (M is a natural number) columns and include N signal converter blocks respectively connected to N row unit output terminals; and M signal converter blocks respectively connected to M column unit output terminals,
   wherein the signal converters each include a first diode having an input terminal connected to an input signal node for receiving one of the plurality of input signals, a second diode having an input terminal connected to the input signal node, and a ground resistor coupled to the input signal node,
   an output terminal of the first diode of each of the signal converters arranged in the same row is connected to one of the row unit output terminals, and
   an output terminal of the second diode of each of the signal converters arranged in the same column is connected to one of the column unit output terminals.

2. The multiplexing signal processing device of claim 1, further comprising:
   a plurality of optical sensors configured to convert a scintillation signal, which is output from a scintillator that converts radiation into the scintillation signal, into an electrical signal,
   wherein the input signal node of each of the signal converters is connected to an output terminal of each of the optical sensors and receives one of output signals of the optical sensors as an input signal.

3. The multiplexing signal processing device of claim 2, further comprising:
   a signal processor configured to identify position information of the optical sensors from which the output signals are output, based on the output signals output by the signal converters.

4. A radiation signal processing device comprising:
   a plurality of optical sensors configured to convert a scintillation signal, which is output from a scintillator unit that converts radiation into the scintillation signal, into an electrical signal; and
   a plurality of signal converters configured to process output signals of the plurality of optical sensors,
   wherein the plurality of signal converters are arranged in a matrix consisting of N (N is a natural number) rows and M (M is a natural number) columns and include N signal converter blocks respectively connected to N row unit output terminals and M signal converter blocks respectively connected to M column unit output terminals, the signal converters each include a first diode having an input terminal connected to an input signal node for receiving one of output signals of the plurality of optical sensors, a second diode having an input terminal connected to the input signal node, and a ground resistor connected to the input signal node, an output terminal of the first diode of each of the signal converters arranged in the same row is connected to one of the row unit output terminals, and an output terminal of the second diode of each of the signal converters arranged in the same column is connected to one of the column unit output terminals.

5. The multiplexing signal processing device of claim 4, further comprising:

a signal processor configured to identify position information of the optical sensors from which the output signals are output, based on the output signals output by the signal converters.

\* \* \* \* \*